United States Patent [19]
Doidge et al.

[11] Patent Number: 5,871,749
[45] Date of Patent: Feb. 16, 1999

[54] THERAPEUTIC TREATMENT OF *H. PYLORI* ASSOCIATED GASTRODUODENAL DISEASE

[75] Inventors: Christopher Vincent Doidge, Box Hill; Adrian Lee, Lane Cove, both of Australia

[73] Assignees: CSL Limited, Parkville; The Univ. of New South Wales, New South Wales, both of Australia

[21] Appl. No.: 464,854

[22] PCT Filed: Jul. 25, 1994

[86] PCT No.: PCT/AU94/00416

§ 371 Date: Aug. 18, 1995

§ 102(e) Date: Aug. 18, 1995

[87] PCT Pub. No.: WO95/03824

PCT Pub. Date: Feb. 9, 1995

[30] Foreign Application Priority Data

Jul. 27, 1993 [AU] Australia ................................ PM0157
Feb. 14, 1994 [AU] Australia ................................ PM3828

[51] Int. Cl.⁶ .................................................. A61K 39/02
[52] U.S. Cl. .................................... 424/234.1; 424/194.1; 435/7.21
[58] Field of Search .................. 424/234.1, 194.1; 435/7.21

[56] References Cited

U.S. PATENT DOCUMENTS

| | | | |
|---|---|---|---|
| 5,370,872 | 12/1994 | Cryz et al. ........................... | 424/194.1 |
| 5,403,924 | 4/1995 | Cover et al. .......................... | 536/23.1 |
| 5,459,041 | 10/1995 | Blaser et al. ......................... | 435/7.21 |
| 5,538,729 | 7/1996 | Czinn et al. .......................... | 424/324.1 |

FOREIGN PATENT DOCUMENTS

| | | |
|---|---|---|
| 4139840A1 | 6/1992 | Germany . |
| 9004030 | 4/1990 | WIPO . |
| WO90/04030 | 4/1990 | WIPO . |
| 9219970 | 11/1992 | WIPO . |
| WO93/16723 | 9/1993 | WIPO . |
| WO93/18150 | 9/1993 | WIPO . |
| WO93/20843 | 10/1993 | WIPO . |
| WO94/09823 | 5/1994 | WIPO . |

OTHER PUBLICATIONS

Czinn et al., Infection and Immunity, 59(7): 2359–2363 (1991).
Czinn et al., Vaccine 11(6): 637–642 (1993).
E. Dick–Hegedus et al., Scand J Gastroenterol 26: 909–915 (1991).
Goodwin et al., Helicobacter Pylori Biology and Clinical Practice, pp. 432–444 (1993).
Lee et al., Gastroenterology 99: 1315–1323 (1990).
O'Connor, Postgrad Med J 68: 549–557 (1992).
Parsonnet et al., The New England Journal of Medicine 325(16): 1127–1131 (1991).
Laszlo et al., Orvosi Hetilap 133: Evfolyam 6. Szam, pp. 359–361 (abstract).
Burke, Vaccine 11(8): 795–804 (1993).
Cox et al., Animal Parasite Control Ulitizing Biotechnology, pp. 49–112 (1992).
Blaser, Clinical Infectious Diseases 15: 386–393 (1992).
Czinn et al, Gastroenterology, vol. 100(Spt 2), A571, May, 1991.
McGhee, J.R. et al, Vaccine, vol. 10(2), 1992, pp. 75–88, 1992.
Clements, J.D. et al, Vaccine vol. 6(3), Jun. pp. 269–277, 1988.
Czinn et al, Infection & Immunity, vol. 59(7), 1991, pp., 2359–2363.
Rappuoli, R et al, Eur. J. Gastroenterol. & Hepatol, 1993, vol. 5 (Suppl 2), pp. 576–578.
Chen, et al (1993, Apr.), Gastroenterology, vol. 104(4), Apr., p(A681).
Genesis Report–DX, Jan. 1993, ISSN:1061–2289.
Chen. M et al (1994) FEMS Microbiology Letters, vol. 116, pp. 245–250.
HP Worldwide Quarterly, 1991–1992, pp. 1–7.
Heap, L. et al., Oct. 7–10, 1991, Microbiol. Ecol. Health Dis., vol. 4, pp. S229.
Dunkley, ML. et al, Microb. Ecol. Health Dis. vol. 4 (Spec. Issue), 1991, p. S148.
Davin, C. et al, Gasteroenterology, vol. 104(4), Apr. 1993, PA1668.
Laszlo, V. et al 1992, vol. 133(6), pp. 359–361, Orvosi Hetilap.
Pavlovskis, OR et al, American Soc. Microbiol, 1991, May 5–9, 1991, p. 119, #E11.
Lee, CK et al, J of Infect. Disease, 1995, vol. 172, pp. 161–172.

*Primary Examiner*—James C. Housel
*Assistant Examiner*—Ginny Allen Portner
*Attorney, Agent, or Firm*—Foley & Lardner

[57] ABSTRACT

The application discloses a method for the treatment of Heliobacter infection in a mammalian host, which comprises administration to said infected host of an immunologically effective amount of one or more Heliobacter antigen(s), optionally in association with a mucosal adjuvant.

20 Claims, No Drawings

THERAPEUTIC TREATMENT OF *H. PYLORI* ASSOCIATED GASTRODUODENAL DISEASE

This Application is a 371 of PCT/AU94/00416 filed Jul. 25, 1994, which claims foreign priority to Australian applications: PM3828, filed Feb. 14, 1994 and PMO157 filed Jul. 27, 1993.

FIELD OF THE INVENTION

This invention relates to the treatment of gastroduodenal disease associated with *Helicobacter pylori* infection and in particular it relates to the use of active immunisation as a treatment for *H. pylori*-associated gastroduodenal disease.

BACKGROUND OF THE INVENTION

The bacterium, *Helicobacter pylori*, is now well established as a major gastroduodenal pathogen, and more than 50% of the world population is infected with this organism which causes gastritis of varying severity. While no symptoms are apparent in a great proportion of infected persons, in a significant number of *H. pylori* infected persons overt disease may result. The majority (95%) of duodenal ulcers are associated with *H. pylori* infection; a causal role is shown by treatment studies which indicate that if the organisms can be eradicated at the time of ulcer healing then the ulcers do not recur—in contrast to 80% recurrence rate at one year in those who remain infected with the organisms. Furthermore, up to 80% of gastric ulcers are thought to be *H. pylori* associated (Blaser, 1992).

There is now increasing evidence of the harmful consequence of long term *H. pylori* infection. In countries such as China, Colombia and Japan the bacterium is picked up very early in life, and in these persons the gastritis slowly progresses until after 30–40 years of continual infection, severe gastric atrophy appears. Gastric atrophy is well documented as being the precursor lesion for gastric cancer, although the actual cancer that develops in an atrophied stomach is dependent on a myriad of other factors including diet. However, all the evidence to date would suggest that the cancer would not develop if it was possible to remove the *H. pylori* infection at an early age before the atrophy had developed (Parsonnet et al., 1991).

There is no laboratory animal model of *H. pylori* infection that can be used for large scale assessment of new anti-*H. pylori* therapies. However, a *Helicobacter felis* mouse model of gastric Helicobacter infection has been developed that has proved extremely useful in the screening of the potential of new antimicrobial therapeutic regimens. *H. felis* is a spiral shaped bacterium that is very closely related to *H. pylori*. This bacterium colonises the stomach of mice in a very similar way to *H. pylori* in the human, i.e. the main ecological niche is gastric mucus and the localisation of colonisation is antral dominant. In germfree mice, *H. felis* infection induces a gastritis that is very similar to the human *H. pylori* infection with a chronic inflammation accompanied by polymorphonuclear leucocyte infiltration. Infection with each organism results in the induction of a similar raised immune response against *H. pylori* and *H. felis* respectively (Lee et al., 1990).

The *H. felis* mouse model has proved to be very predictive of the efficacy of anti-*H. pylori* agents in humans. Thus, monotherapy with agents with high in vitro activity such as erythromycin show no significant in vivo effect against *H. felis* in mice, just as erythromycin has no anti-*H. pylori* effect in humans despite high antimicrobial effects in vitro. In contrast, the triple therapy regimens of a bismuth compound, metronidazole, and tetracycline or amoxycillin lead to a very high eradication rate in *H. felis* infected mice (Dick-Hegedus and Lee, 1991). Such triple therapies are the most successful human anti-*H. pylori* regimens, and at the present time are recommended as the first choice for anti-*H. pylori* therapy. However, established Helicobacter infections are difficult to treat, and current chemotherapeutic regimens remain suboptimal due to problems with efficacy, toxicity, drug resistance and reinfection (O'Connor, 1992).

Active immunisation of already infected patients has not been proven efficacious for any clinically manifest human infectious disease (Burke, 1992). Given that *H. pylori* infections persist for long periods, if not the life of the infected individual, despite the presence of a vigorous immune response that includes a high level of circulating IgG antibody in the serum and the demonstration of local specific IgA antibody in the gastric mucosa, it has been considered that active immunisation was unlikely to be effective in therapy (Goodwin, 1993). Indeed, Czinn et al. (1993) in proposing that oral vaccination may be a feasible approach for the prevention of *H. pylori* infection in humans (based on an evaluation of an oral immunisation protocol in the *H. felis* mouse model), suggested that once infection is established neither antibody nor antibiotics are very effective at eradication.

Varga et al. (1992) have reported that a *H. pylori* vaccine prepared from organisms derived from a patient, and injected parenterally into that patient, resulted in an allergic reaction and failure to eradicate the organism.

Surprisingly, it has now been discovered for the first time that there is indeed a therapeutic potential for active immunisation against gastric Helicobacter infection. Furthermore, it has been discovered that oral administration of *H. pylori* antigen, with a suitable mucosal adjuvant, does not result in allergic or hypersensitivity symptoms, but results in suppression or eradication of the infecting organisms from the gastric mucosa.

SUMMARY OF THE INVENTION

According to one aspect of the present invention, there is provided a method for the treatment of Helicobacter infection in a mammalian host, which comprises the oral administration to said infected host of an immunologically effective amount of one or more Helicobacter antigen(s), optionally in association with a mucosal adjuvant.

In another aspect, there is provided a vaccine composition for the treatment of Helicobacter infection in a mammalian host, which comprises an immunologically effective amount of one or more Helicobacter antigen(s), optionally in association with a mucosal adjuvant.

In yet another aspect, the present invention provides the use of a vaccine composition comprising an immunologically effective amount of one or more Helicobacter antigen(s), optionally in association with a mucosal adjuvant, in the treatment of Helicobacter infection in a mammalian host.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

By use of the term "immunologically effective amount" herein, it is meant that the administration of that amount to an individual infected host, either in a single dose or as part of a series, is effective for treatment of Helicobacter infection. This amount varies depending upon the health and physical condition of the individual to be treated, the taxonomic group of individual to be treated, the capacity of the individual's immune system to synthesise antibodies, the degree of protection desired, the formulation of the vaccine, the assessment of the medical situation, and other relevant factors. It is expected that the amount will fall in a relatively broad range that can be determined through routine trials.

DETAILED DESCRIPTION OF THE INVENTION

The Helicobacter antigen(s) used in accordance with the present invention may be *H. felis* antigen(s), or more preferably *H. pylori* antigen(s). In a particularly preferred aspect of the present invention, a vaccine composition comprising *H. pylori* antigen(s) in association with a mucosal adjuvant is used in the treatment of *H. pylori* infection in a human patient.

Preferably, the Helicobacter antigen(s) comprise a bacterial sonicate, and in particular a *H. pylori* sonicate. More preferably, the Helicobacter antigen(s) used in accordance with the present invention comprise inactivated whole bacterial cells of *H. pylori*.

Alternatively, the Helicobacter antigen(s) used in accordance with the present invention may comprise one or more individual antigens, particularly one or more *H. pylori* antigens such as *H. pylori* urease, or *H. pylori* cytotoxin (CT), Cytotoxin Associated Immunodominant (CAI) antigen or heat shock protein (hsp) as disclosed by way of example in International Patent Publication No. WO 93/18150.

One mucosal adjuvant which is optionally, and preferably, administered with the Helicobacter antigen(s) to the infected host is cholera toxin. Another preferred mucosal adjuvant which may be administered with the Helicobacter antigen(s) is *E. coli* heat labile toxin (*E. coli* HLT). Mucosal adjuvants other than cholera toxin and *E. coli* HLT which may be used in accordance with the present invention include non-toxic derivatives of cholera toxin, such as the B sub-unit (CTB), chemically modified cholera toxin, or related proteins produced by modification of the cholera toxin amino acid sequence. Each of these molecules with mucosal adjuvant or delivery properties may be added to, or conjugated with, the Helicobacter antigen(s). Other compounds with mucosal adjuvant or delivery activity may be used, such as: bile; polycations such as DEAE-dextran and polyornithine; detergents such as sodium dodecyl benzene sulphate; lipid-conjugated materials; antibiotics such as streptomycin; vitamin A; and other compounds that alter the structural or functional integrity of mucosal surfaces. Other mucosally active compounds include derivatives of microbial structures such as MDP; acridine and cimetidine.

Helicobacter antigen(s) may be delivered in accordance with this invention in ISCOMS (immune stimulating complexes), ISCOMS containing CTB, liposomes or encapsulated in compounds such as acrylates or poly(DL-lactide-co-glycoside) to form microspheres of a size suited to adsorption by M cells. Alternatively, micro or nanoparticles may be covalently attached to molecules such as vitamin B12 which have specific gut receptors. Antigen(s) may also be incorporated into oily emulsions and delivered orally. An extensive though not exhaustive list of adjuvants can be found in Cox and Coulter, 1992.

Other adjuvants, as well as conventional pharmaceutically acceptable carriers, excipients, buffers or diluents, may also be included in the therapeutic vaccine composition of this invention. The vaccine composition may, for example, be formulated in enteric coated gelatine capsules including sodium bicarbonate buffers together with the Helicobacter antigen(s) and mucosal adjuvant.

Generally, a vaccine composition in accordance with the present invention will comprise an immunologically effective amount of Helicobacter antigen(s), and optionally a mucosal adjuvant, in conjunction with one or more conventional pharmaceutically acceptable carriers and/or diluents. As used herein "pharmaceutically acceptable carriers and/or diluents" include any and all solvents, dispersion media, aqueous solutions, coatings, antibacterial and antifungal agents, isotonic and absorption delaying agents and the like. The use of such media and agents for pharmaceutical active substances is well known in the art and is described by way of example in *Remington's Pharmaceutical Sciences*, 18th Edition, 1990, Mack Publishing Company, Pennsylvania, U.S.A.

The pharmaceutical composition of this invention may be orally administered directly to the mammalian host, for example, with an inert diluent or with an assimilable edible carrier, or it may be enclosed in hard or soft shell gelatine capsule, or it may be compressed into tablets, or it may be incorporated directly with the solid or liquid food of the diet. For oral therapeutic administration, the active compound may be incorporated with excipients and used in the form of ingestible tablets, buccal tablets, troches, capsules, elixirs, suspensions, syrups, wafers, and the like. The percentage of active component in the compositions and preparations may of course be varied and is such that a suitable dosage will be obtained to be immunologically effective.

Solid oral dosage units such as tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active component, sucrose as a sweetening agent, methyl and prophylparabens as preservatives, a dye and flavouring such as cherry or orange flavour. Of course, any material used in preparing any dosage unit form should be pharmaceutically pure and substantially non-toxic in the amounts employed.

The vaccine composition of the invention is administered orally in amounts readily determined by persons of ordinary skill in this art. Thus, for adults a suitable dosage would be in the range of 10 μg to 10 g, for example 50 μg to 3 g. Similar dosage ranges would be applicable for children.

As noted above, a suitable mucosal adjuvant is cholera toxin. The amount of mucosal adjuvant employed depends on the type of mucosal adjuvant used. For example, when the mucosal adjuvant is cholera toxin, it is suitably used in an amount of 10 nanogram to 50 μg, for example 01 μg to 10 μg. When the mucosal adjuvant is *E. coli* heat labile toxin, suitable amounts are 1 μg to 1 mg, for example 5 μg to 50 μg.

In work leading to the present invention, active immunisation of mice previously infected with *H. felis,* with oral doses of cholera toxin or *E. coli* HLT adjuvant and a whole cell H. felis or H. pylori sonicate, result in the clearance of H. felis from the gastric mucosa. It is therefore anticipated that active immunisation of infected humans with oral doses of a mucosal adjuvant with H. pylori antigen(s) will result in the clearance of H. pylori from the gastric mucosa. Based on previous studies with this model using anti-H. pylori agents, it is considered that this is the first evidence of the therapeutic potential of active immunisation with H. pylori vaccines, and indicates that a vaccine composition for the therapy of human H. pylori-associated gastroduodenal disease is a preparation of Helicobacter antigen(s), optionally and preferably combined with a mucosal adjuvant.

It will be apparent to persons skilled in the field that effective treatment of Helicobacter pylori infection in humans with an oral vaccine composition of Helicobacter antigen(s) which will eradicate or suppress the infection will provide a significant therapeutic benefit via the suppression or elimination of gastritis, prevention of peptic ulcer relapse and reduction in the harmful sequelae of Helicobacter pylori infection including peptic ulceration and gastric cancer.

The present invention is further illustrated in the following, non-limiting Examples.

EXAMPLE 1

One hundred and sixty female SPF mice from the Animal Breeding Unit of the University of New South Wales, Australia, were infected with four oral doses of $10^9$–$10^{10}$ living Helicobacter felis (ATCC culture 49179) given two days apart.

Bacteria were grown in plastic Petri dishes on Blood Agar Base No. 2, 3.8% w/v (Oxoid, Basingstoke, U.K.) with 7% v/v whole horse blood (Oxoid), containing amphotericin B (Fungizone, Squibb, Princeton, N.J., USA) 2.5 mg/l; trimethoprim (Sigma, St.Louis, Mo., USA), 10 mg/l. Plates were incubated in a microaerophilic humid atmosphere (Oxoid, BR56) at 37° C. for 48 hours.

Sonicates were prepared by growth of the organisms, as described above, followed by harvesting of the organisms in 0.1 molar phosphate buffered saline (PBS). The cells were washed, collected by centrifugation, washed once in PBS, and resuspended in fresh PBS. The cells were then sonicated at the rate of one minute per ml of cell suspension (50% duty cycle) using a B-30 Branson Cell Disrupter. The sonicate was stored at −20° C.

On days 28, 42, 44 and 47 after administration of the last infecting dose of H. felis, 20 of the mice were given orally 0.2 ml of a suspension containing 10 $\mu$g of cholera toxin (Sigma C 3012) and a sonicate of H. felis containing 1 mg protein (BIO-RAD DC protein assay).

Samples of antral mucosa were tested for infection using a rapid microtitre urease test as described previously (Lee et al., 1990). This test has been validated as being highly predictive of H. felis gastric infection. Groups of 40 mice (20 vaccinates and 20 controls) were euthanased at intervals of 1 week, 1 month, 2 months and 3 months after the last dose of vaccine.

The results are shown in Table 1.

These results show that treatment of H. felis infected mice with an oral vaccine comprised of Helicobacter antigens and a mucosal adjuvant, results in cure of the infection in a significant proportion of mice. This effect is evident 1 week after cessation of therapy, and continues for at least 3 months, demonstrating that the mice have been cured of their infection.

TABLE 1

| Immunisation | Proportion of H. felis infected mice | | | |
| --- | --- | --- | --- | --- |
| | 1 week | 1 month | 2 months | 3 months |
| Nil | 19/19 | 20/20 | 18/19 | 13/19 |
| Sonicate plus CT | 2/20 | 3/20 | 6/20 | 1/17 |
| | $P < 0.0001$* | $P < 0.0001$ | $P < 0.05$ | $P < 0.0001$ |

*Fisher's exact test (two tailed).

EXAMPLE 2

One hundred female BALB/c mice from the Animal Breeding Unit of the University of New South Wales, Australia, were infected with 3 oral doses of $10^8$ living Helicobacter felis (ATCC culture 49179) given 2 days apart, i.e. days 1, 3 and 5.

Bacteria were grown in plastic Petri dishes on Blood Agar Base No. 2, 3.8% w/v (Oxoid, Basingstoke, U.K.) with 7% v/v whole horse blood), (Oxoid), containing amphotericin B (Fungizone, Squibb, Princeton, N.J., USA) 2.5 mg/l; trimethoprim (Sigma, St.Louis, Mo., USA), 10 mg/l. Plates were incubated in a microaerophilic humid atmosphere (Oxoid, BR56) at 37° C. for 48 hours.

Sonicates were prepared by growth of the organisms, as described above, followed by harvesting of the organisms in 0.1 molar phosphate buffered saline (PBS). The cells were washed collected by centrifugation, washed once in PBS, and resuspended in fresh PBS. The cells were then sonicated at the rate of one per minute per ml of cell suspension (50% duty cycle) using a B-30 Branson Cell Disrupter. The sonicate was stored at −20° C.

On days 21, 35, 37, and 40 after administration of the last infecting dose of H. felis, 20 mice were each given orally 0.2 ml of a solution containing 10 $\mu$g of cholera toxin (Sigma C 3012), 20 mice were each given orally 0.2 ml of a suspension containing 10 $\mu$g of cholera toxin and a sonicate of H. felis containing 1 mg protein (BIO-RAD DC protein assay), 20 mice were each given orally 0.2 ml of a suspension containing a sonicate of H. felis containing 1 mg protein, 20 mice were each given orally 0.2 ml of a suspension containing 10 $\mu$g of cholera toxin and a sonicate of H. pylori (strain 921023) containing 1 mg protein, and 20 mice were not orally vaccinated.

One week after the final immunising dose all the mice were euthanased. Samples of antral mucosa were tested for infection using a rapid microtitre urease test as described previously (Lee et al., 1990). This test has been validated as being highly predictive of H. felis gastric infection.

The results are shown in Table 2.

These results show that oral administration of Helicobacter antigens derived from either H. felis, or H. pylori along with a mucosal adjuvant, will cure a significant portion of H. felis infected mice.

TABLE 2

| Vaccine | Number of animals infected | Significance |
| --- | --- | --- |
| Nil | 16/20 | |
| CT alone | 15/20 | N.S. |
| H. felis sonicate alone | 12/20 | N.S. |
| H. felis sonicate plus CT | 8/19 | $P < 0.05$* |
| H. pylori sonicate plus CT | 4/20 | $P < 0.001$ |

*Fisher's exact test (two tailed)

EXAMPLE 3

One hundred female SPF mice from the Animal Breeding Unit of the University of New South Wales, Australia, were infected with 4 oral doses of $10^9$–$10^{10}$ living *Helicobacter felis* (ATCC culture 49179) given 2 days apart. 20 female SPF mice were left uninfected, as negative controls.

Bacteria were grown in plastic Petri dishes on Blood Agar Base No. 2, 3.8% w/v (Oxoid, Basingstoke, UK) with 7% v/v whole horse blood (Oxoid), containing amphotericin B (Fungizone, Squibb, Princeton, N.J., USA) 2.5 mg/l; trimethoprim (Sigma, St.Louis, Mo., USA), 10 mg/l. Plates were incubated in a microaerophilic humid atmosphere (Oxoid, BR56) at 37° C. for 48 hours.

Sonicates were prepared by growth of the organisms, as described above, followed by harvesting of the organisms in 0.1 molar phosphate buffered saline (PBS). The cells were washed, collected by centrifugation, washed once in PBS, and resuspended in fresh PBS. The cells were then sonicated at the rate of one per minute per ml of cell suspension (50% duty cycle) using a B-30 Branson Cell Disrupter. The sonicate was stored at -20° C.

Starting between 6 weeks and 9 weeks after their last infecting dose of *H. felis*, 20 mice were each given orally 0.2 ml of a solution containing 25 μg of *E. coli* heat labile toxin (HLT) (Sigma E 8015), 20 mice were each given orally 0.2 ml of a suspension containing 25 μg of HLT and a sonicate of *H. pylori* containing 1 mg protein (BIO-RAD DC protein assay), 20 mice were each given orally 0.2 ml of a suspension containing a sonicate of *H. pylori* containing 1 mg protein, and 40 mice were not orally vaccinated.

Each group received three further doses 15, 17 and 20 days after their initial dose.

Four weeks after the final immunising dose all the mice were euthanased. Samples of antral mucosa were tested for infection using a rapid microtitre urease test as described previously (Lee et al., 1990). This test has been validated as being highly predictive of *H. felis* gastric infection.

The results are shown in Table 3.

They show that oral administration of Helicobacter antigens derived from *H. pylori* along with a mucosal adjuvant *E. coli* heat labile toxin, will cure a significant portion of *H. felis* infected mice.

TABLE 3

| Treatment Group | Proportion of *H. felis* infected mice. |
|---|---|
| Uninfected, unvaccinated | 0/20 |
| Infected, unvaccinated | 40/40 |
| Infected, Hp antigen alone | 20/20 |
| Infected, *E. coli* HLT alone | 20/20 |
| Infected, Hp antigen & HLT | 6/19* |

*$P < 0.0001$ (Fisher's exact test, two tailed).

REFERENCES

Blaser, M. J. (1992). *Helicobacter pylori:* Its role in disease. *Clin. Infect. Dis.* 15, 386–393.

Burke, D. S. (1993). Of postulates and peccadilloes: Robert Koch and vaccine (tuberculin) therapy for tuberculosis. *Vaccine,* 11, 795–804.

Cox, J. and Coulter, A. (1992). Advances in Adjuvant Technology and Application. In Animal Parasite Control Utilising Biotechnology. Edited W. K. Yong, CRC Press.

Czinn, S. J., Cai, A. and Nedrud, J. G. (1993). Protection of germ-free mice from infection by *Helicobacter felis* after active oral or passive IgA immunization. *Vaccine,*11, 637–642.

Dick-Hegedus, E. and Lee, A. (1991). Use of a mouse model to examine anti-*Helicobacter pylori* agents. *Scand. J. Gastrolenterol.* 26, 909–915.

Goodwin, C. S. (1993). Overview of *Helicobacter pylori* gastritis, peptic ulcer, and gastric cancer and the possible development of an *H. pylori* vaccine. *In Helicobacter pylori* Biology and Clinical Practice. Edited by Goodwin and Worsley. CRC Press.

Lee, A., Fox, J. G., Otto, G. and Murphy, J. (1990). A small animal model of human *Helicobacter pylori* active chronic gastritis. *Gastroenterology,* 99, 1316–1323.

O'Connor, H. J. 91992). Eradication of *Helicobacter pylori:* Therapies and clinical implications. *Postgrad. Med. J.* 68, 549–557.

Parsonnet, J., Friedman, G. D., Vandersteen, D. P., Chang, Y., Vogelman, H. J., Orentreich, N. and Sibley, R. K. (1991). *Helicobacter pylori* infection and the risk of gastric carcinoma. *N. Engl. J. Med.* 325, 1127–1131.

Varga, L., Löcsei, Z., Döbrönte, Z., Lakatos, F., Brözik, M. and Meretey, K. (1992). *Helicobacter pylori* allergy. *Orv. Hetil.* 133, 359–361.

We claim:

1. A method for the treatment of a pre-existing Helicobacter infection in a mammalian host, which comprises mucosal administration to the infected host of (a) an immunologically effective amount of one or more Helicobacter antigens, in association with (b) a mucosal adjuvant, wherein said administration of (a) in association with (b) eradicates or suppresses the pre-existing infection in the host.

2. A method according to claim 1, wherein said one or more Helicobacter antigens comprise one or more *H. pylori* antigens.

3. A method according to claim 1, wherein said one or more Helicobacter antigens comprise one or more *H. felis* antigens.

4. A method according to claim 1, wherein said one or more Helicobacter antigens are provided by a sonicate of Helicobacter cells.

5. A method according to claim 1, wherein said adjuvant is cholera toxin or *E. coli* heat labile toxin.

6. A method according to claim 1, wherein said infected host is an infected human.

7. A method according to claim 1, wherein the mucosal adjuvant has mucosal delivery activity.

8. A method according to claim 1, further comprising the step of detecting a therapeutic effect in said infected host.

9. A method according to claim 1, further comprising administration of an antibiotic to the infected host.

10. A method for the treatment of a pre-existing Helicobacter infection in a mammalian host, which comprises oral administration to the infected host of (a) an immunologically effective amount of one or more Helicobacter antigens, in association with (b) a mucosal adjuvant, wherein said administration of (a) in association with (b) eradicates or suppresses the pre-existing infection in the host.

11. A method according to claim 10, wherein said one or more Helicobacter antigens comprise one or more *H. pylori* antigens.

12. A method according to claim 10, wherein said one or more Helicobacter antigens comprise one or more *H. felis* antigens.

13. A method according to claim 10, wherein said one or more Helicobacter antigens are provided by a sonicate of Helicobacter cells.

14. A method according to claim 10, wherein said adjuvant is cholera toxin or *E. coli* heat labile toxin.

15. A method according to claim 10, wherein said infected host is an infected human.

16. A method according to claim 10, wherein the mucosal adjuvant has mucosal delivery activity.

17. A method according to claim 10, further comprising the step of detecting a therapeutic effect in said infected host.

18. A method according to claim 10, further comprising administration of an antibiotic to the infected host.

19. A method according to claim 11, wherein said one or more Helicobacter antigens is selected from the group consisting of *H. pylori* urease, *H. pylori* cytotoxin, *H. pylori* cytotoxin associated immunodominant antigen, and *H. pylori* heat shock protein.

20. A method according to claim 10, wherein said one or more Helicobacter antigens is selected from the group consisting of *H. pylori* urease, *H. pylori* cytotoxin, *H. pylori* cytotoxin associated immunodominant antigen, and *H. pylori* heat shock protein.

* * * * *